United States Patent [19]

Torii et al.

[11] 4,148,697

[45] Apr. 10, 1979

[54] PREPARATION OF TETRAALKYLTHIURAM DISULFIDES

[75] Inventors: Sigeru Torii; Hideo Tanaka; Kiyoshi Mishima, all of Okayama, Japan

[73] Assignee: Ouchi Shinko Kagaku Kogyo Kabushiki Kaisha, Tokyo, Japan

[21] Appl. No.: 874,177

[22] Filed: Feb. 1, 1978

[30] Foreign Application Priority Data

Jan. 29, 1977 [JP] Japan ................................ 52-8230

[51] Int. Cl.² .................... C25B 3/02; C07C 155/10
[52] U.S. Cl. .................................. 204/78; 204/72; 204/59 R; 260/567
[58] Field of Search .................. 204/72, 78, 59 R; 260/567

[56] References Cited

U.S. PATENT DOCUMENTS

| | | | |
|---|---|---|---|
| 3,116,328 | 12/1963 | Cox | 260/567 |
| 3,193,580 | 7/1965 | Werres et al. | 260/567 |
| 3,255,250 | 6/1966 | Budd et al. | 260/567 |
| 3,472,747 | 10/1969 | Smith | 204/72 |

FOREIGN PATENT DOCUMENTS 6309269 6/1963 Japan ........................................ 260/567

*Primary Examiner*—F.C. Edmundson
*Attorney, Agent, or Firm*—Ladas, Parry, Von Gehr, Goldsmith & Deschamps

[57] ABSTRACT

A tetraalkylthiuram disulfide is prepared in a higher yield without formation of by-products by subjecting the corresponding alkali metal dialkyldithiocarbamate to electrolytic oxidation, which is carried out in a two-layer electrolytic solution consisting essentially of either (1) water and carbon disulfide or (2) water and a mixture of carbon disulfide and a halogenated alkane of higher density than water, the carbon disulfide being predominant in the mixture, by means of electrodes placed in the aqueous layer containing the dialkyldithiocarbamate. The resulting disulfide is extracted to the lower layer of the electrolytic solution and is recovered from the layer. The dialkyldithiodicarbamate can be continuously produced in situ by adding carbon disulfide and dialkylamine gradually to the aqueous layer of the electrolytic solution, which contains an alkalimetal hydroxide produced during the electrolytic oxidation of the dialkyldithiocarbamate.

10 Claims, No Drawings

PREPARATION OF TETRAALKYLTHIURAM DISULFIDES

BACKGROUND OF THE INVENTION

1. Field of the Invention

This invention relates to a novel process for preparation of tetraalkylthiuram disulfides. More particularly, it relates to the process for preparing the disulfides characterized in that an aqueous solution containing an alkali metal dialkyldithiocarbamate is subjected to electrolytic oxidation in the presence or absence of a supporting electrolyte, which aqueous layer is placed over a layer consisting essentially of carbon disulfide or a mixed solvent of carbon disulfide as a predominant component and a halogenated alkane having a higher density than water, to obtain directly the corresponding tetraalkylthiuram disulfide.

2. Description of the Prior Art

A typical industrial process for production of tetraalkylthiuram disulfides to be used as vulcanizing accelerators or agents is as follows. An aqueous solution of a sodium dialkyldithiocarbamate is prepared by reacting the corresponding dialkylamine and carbon disulfide at a low temperature in the presence of an aqueous sodium hydroxide solution. The resulting aqueous solution is purified, and then sulfuric acid and hydrogen peroxide used as an oxidizing agent are dropwisely added thereto to effect neutralization and oxidation of the dialkyldithiocarbamic acid. The resulting precipitate of the end product is subjected to filtration, washing with water, dehydration, drying, and grinding if so desired.

In the oxidative dimerization of sodium dialkyldithiocarbamates, oxidizing agents such as nitrogen dioxide ($NO_2$), chlorine ($Cl_2$), iodine ($I_2$), ozone ($O_3$), oxygen ($O_2$), sodium nitrite ($NaNO_2$), sodium hypochlorite ($NaOCl$), sulfur monochloride ($S_2Cl_2$), sulfur dichloride ($SCl_2$), potassium perbromate ($KBrO_3$), selenic acid ($H_2SeO_3$) and ammonium persulfate [$(NH_4)_2S_2O_8$] can be employed instead of hydrogen peroxide. It should be noted that in those oxidative processes in which oxidizing agents are used, the stoichiometric quantities of oxidizing agents, neutralizing agents and the like are required, and special handling care must be taken as to the reaction apparatus and accessory apparatus as well as the process controls of the reaction.

On the other hand, a process for preparing tetraalkylthiuram disulfides via direct electrolytic oxidation of the corresponding alkali metal dialkyldithiocarbamates, in which use of the oxidizing agents and the like is avoided, is disclosed in U.S. Pat. No. 2,385,410. In this electrolytic oxidation process, the electrolytic reaction is carried out at a comparatively high temperature of 50° to 60°. It is well known that tetraalkylthiuram disulfides are generally inferior in thermal stability. The resulting disulfide could be partially decomposed thermally at a reaction temperature of 50° to 60° C., and the yield and quality of the product could thus be lowered.

SUMMARY OF THE INVENTION

An object of the present invention is to provide a novel process for preparing tetraalkylthiuram disulfides via electrolytic oxidation in a high yield.

Another object of the present invention is to provide a process for preparing the disulfides without forming by-products and discharging pollutants outside.

Still another object of the present invention is to provide an efficient process for continuously preparing the sulfides via electrolytic oxidation.

Other objects of the present invention will be made clear in the following descriptions.

According to this invention, briefly summarized, there is provided a novel process for preparation of a tetraalkylthiuram disulfide, which comprises subjecting an aqueous solution containing an alkali metal dialkyldithiocarbamate wherein the alkali metal is sodium, potassium or lithium to electrolytic oxidation to form the corresponding tetraalkylthiuram disulfide as shown in the reaction formula

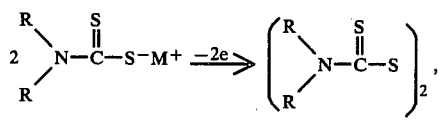

wherein R represents an alkyl group having 1 to 4 carbon atoms, and M represents an alkali metal, said electrolytic oxidation being conducted at approximately room temperature in the absence or presence of a supporting electrolyte by inserting electrodes in an aqueous layer of a two-layer electrolytic solution consisting essentially of either (1) water as an aqueous upper layer or phase and carbon disulfide as a non-aqueous lower layer or phase or (2) water as an aqueous upper layer or phase and a mixture containing carbon disulfide as a predominant component and a halogenated alkane as a non-aqueous lower layer or phase and passing electric current at a suitable terminal voltage for producing the sulfide for a time necessary to complete the reaction; allowing the resulting tetraalkylthiuram disulfide to be extracted into the lower layer comprising carbon disulfide; taking out the extractant layer; and removing the solvent(s) of the layer.

DESCRIPTION OF THE PREFERRED EMBODIMENTS

Solvent

The solvents suitable for use in the present invention can be conveniently classified into two groups.

The first group is water which is used as an actual electrolytic solvent.

The second group includes a hydrophobic solvent which is carbon disulfide, or a mixture containing carbon disulfide as a predominant component of the mixture and an appropriate quantity of a halogenated alkane having higher density than water such as chloroalkanes of $C_1$ to $C_3$, preferably of $C_1$ to $C_2$, e.g., dichloromethane, chloroform, dichloroethane, trichloroethane and methyl or ethyl trichloroacetate. The mixture is hereinafter referred to as "mixed solvent." These halogenated alkanes can be used in mixture with carbon disulfide in a desired proportion to improve the extracting effect of carbon disulfide of the reaction product, preferably in a quantity from 0.1 to 20 times by volume that of the carbon disulfide. The halogenated alkanes should preferably be those in which tetraalkylthiuram disulfides are soluble and which are miscible with carbon disulfide to form homogeneous mixtures.

Supporting Electrolyte

A supporting electrolyte is not especially required in the present invention since an alkali metal salt of dialkyldithiocarbamic acid is employed as the starting material. An appropriate supporting electrolyte, however, can be used if so desired. Representative examples of supporting electrolytes include perchlorates such as lithium perchlorate, magnesium perchlorate, and quaternary alkylammonium perchlorates; perborate such as quaternary alkylammonium tetrafluoroborates, quaternary alkylammonium halides, alkali metal halides, quaternary alkylammonium nitrates; and quaternary alkylammonium para-toluenesulfonates, wherein the alkyl group is methyl, ethyl, a propyl or a butyl, the alkali metal is lithium, potassium or sodium, and halogen is chlorine, bromine or iodine. As to the roles and embodiments of supporting electrolytes, reference is made to C. K. Mann: Electroanal. Chem. 16 157 (1969), cited herein by reference.

Electrodes

The electrodes to be employed in the present invention include commercial electrodes for electrolytic use produced from platinum or carbon, electrodes which have been fabricated into an electrode form from carbon, titanium oxide or other electroconductive metal oxide materials, and these electrodes whose surfaces have been subjected to special processes.

It should be noted that the mixed solvents, supporting electrolyte, and electrodes to be employed in the present invention are not restricted to the examples illustrated above.

Reaction and Recovery

The electrolytic oxidation reaction according to the present invention is conducted by using a two-layer electrolytic solution which consistes essentially of an upper layer comprising an aqueous solution of an alkali metal dialkyldithiocarbamate and a lower layer comprising carbon disulfide, preferably with an aqueous layer to which an appropriate supporting electrolyte is added if desired in an amount of 0.01 to 0.5 mol/liter.

Electrolysis is carried out under stirring by means of electrodes such as platinum or carbon electrodes inserted into the aqueous layer. Tetraalkylthiuram disulfide can be continuously produced when carbon disulfide and dialkylamine corresponding to the alkali metal dialkyldithiocarbamate consumed in the reaction are supplementally added and the electrolysis is continued. The reaction product is extracted by the lower layer comprising carbon disulfide. When the resulting product has reached a suitable concentration, the lower layer is taken out and the solvent is removed to obtain the end product, a tetraalkylthiuram disulfide.

The reaction conditions of the electrolytic oxidation differ depending on the type of the electrolytic cell, the kind of the amine to be used, and the like. The electrolytic reaction in the two-layer solution according to the present invention can be conducted under the conditions of electric current density and potential which are generally employed in the aft. A feature of the present invention is that, by merely carrying out electrolysis by maintaining a constant terminal voltage of 1.0 to 10 V, preferably 1.5 to 3.0 V, only the objective product can be efficiently obtained. Electrolytic oxidation at a constant terminal voltage can assure the use of a simple electrolytic apparatus and operation. The preferred current density is in the range of 100 to 0.1 mA/cm$^2$.

In general, when electrolysis is conducted at a constant terminal voltage, some fluctuation occurs in the electrode potential. If a voltage which is somewhat higher than the preferred voltage is employed in the electrolytic reaction, undesirable by-products may also be formed. Formation of such by-products is increased under these electrolysis conditions especially when carbon electrodes which are highly adsorptive are employed. In the present invention, however, electrolysis is carried out in the two-liquid system consisting essentially of an upper aqueous layer and a lower extractant, and the resulting product moves rapidly to the extractant layer. The side reaction which is due to some fluctuation of electrode potential can be avoided by the cleaning effect of the electrode surfaces owing to occasional contact of the extractant solvent with the electrode surfaces. Therefore, a broad range of terminal voltage can be employed in the present invention.

The reaction temperature is in the range of 5° to 40° C., preferably 10° to 30° C.

The lower or hydrophobic solvent layer containing the resulting electrolytic product is subjected to washing with water and dehydration, if desired, and then stripping of the extractant solvent and low-boiling volatile components to obtain a tetraalkylthiuram disulfide in a yield of 98 to 100%.

The production process according to the present invention can be carried out by either a continuous system or a batch system. The hydrophobic solvent and excess dialkylamine or excess carbon disulfide can be recovered as distillates when the solvents are stripped. The aqueous layer containing an alkali metal dialkyldithiocarbamate and a supporting electrolyte can be supplied to the electrolytic reaction as it is. In the continuous reaction system, the advantage in a very long-run operation can be exhibited since dialkylamine and carbon disulfide in a predetermined proportion are added to the reaction system when necessary, and the resulting product can be continuously separated from the hydrophobic solvent layer.

Also, according to the process of the present invention, an alkali metal hydroxide produced in the course of reaction reacts with the supplemented dialkylamine and carbon disulfide and is consumed to form the corresponding alkali metal dialkyldithiocarbamate. Therefore, the alkali metal hydroxide can be automatically recycled and used, and the pH in the reaction system is maintained approximately at a constant level.

The present process can be carried out without a neutralizing agent and at a temperature near room temperature. Furthermore, a supporting electrolyte can be used without replenishment since the electrolyte remains in the reaction system as it is. Moreover, little or no side reaction takes place. Thus, tetraalkylthiuram disulfides can be obtained in a very good yield as high as 98 to 100% according to the present invention.

According to the process of the present invention, the aqueous layer in which the electrolytic reaction takes place is recycled and is not discharged outside. Furthermore, the extractant solvent containing the end product is recovered by simply stripping it and can be recycled to the electrolytic reaction system. Thus, the present invention has been proved to be suitable for producing tetraalkylthiuram disulfides on an industrial scale, since the environmental pollution problems due to waste water containing the conventional by-products are eliminated by the present invention.

The inventio will be understood more fully by reference to the following examples, which are intended to illustrate the present invention and are not to be construed to limit the scope of the invention.

EXAMPLE 1

Preparation of tetramethylthiuram disulfide in a water-carbon disulfide-dichloromethane solvent system In a 50-ml branched test tube is placed 500 mg (3.5 millimols) of sodium dimethyldithiocarbamate, followed by addition thereto of 20 ml of water to prepare a homogeneous aqueous solution. The solution is further supplied with 5 ml of methylene chloride and 1 ml of carbon disulfide. The test tube is then equipped with a stirrer and a thermometer as well as platinum electrodes (1.5 cm × 2 cm in dimension) which are inserted into the aqueous layer. Electrolysis is carried out with stirring under the conditions of a terminal voltage of 2 V and a current density of 10 to 5 mA/cm², while the reaction temperature is maintained at 15° to 20° C. The electrolysis is continued by adding 0.04 ml (0.3 millimol) of 50% aqueous dimethyl amine solution and 23 mg (0.3 millimol) of carbon disulfide for every quantity of electricity of $0.3 \times 10^{-3}$F passed through the reaction system. Electrolysis is discontinued when a total quantity of electricity of $5 \times 10^{-3}$F has been passed. The lower layer of the reaction system is taken out and subjected to washing with water, dehydration and concentration. In one actual instance of practice, 595 mg of the tetramethylthiuram disulfide (yield 99%) was obtained as white powdery crystals having a melting point of 146.0° C. The resulting product was confirmed to be tetramethylthiuram disulfide as a result of the identification by thin-layer chromatography and infrared (IR) and nuclear magnetic resonance (NMR) absorption spectra as well as a mixed melting point test with a standard sample thereof.

EXAMPLE 2

Preparation of tetraethylthiuram disulfide in a water-carbon disulfide solvent system The experiment was carried out similarly as in Example 1. The reaction system was prepared by dissolving 500 mg (2.92 millimols) of potassium diethyldithiocarbamate and 100 mg of sodium perchlorate used as a supporting electrolyte in 20 ml of water, followed by addition thereto of 5 ml of carbon disulfide. Electrolytic reaction was carried out by using carbon electrodes (3 cm × 2 cm in dimension) at a reaction temperature of 12° to 14° C. with stirring under the conditions of a terminal voltage of 2 V and a current density of 10 to 5 mA/cm², during which diethylamine [67 mg (0.5 millimol) × 10 times] was intermittently added and a quantity of electricity of $5 \times 10^{-3}$F was passed. The lower layer of carbon disulfide solution was taken out and subjected to washing with water, dehydration, and concentration.

Thus, 733 mg (yield 99%) of the tetraethylthiuram disulfide was obtained as slightly grayish white powdery crystals having a melting point of 70.5° C. The resulting product was confirmed to be tetraethylthiuram disulfide as a result of the identification by thin-layer chromatography and IR and NMR absorption spectra as well as a mixed melting point test with a standard sample thereof.

EXAMPLE 3

Preparation of tetrabutylthiuram disulfide in a water-carbon disulfide system The experiment was carried out by using platinum electrodes (2 cm × 3 cm) similarly as in Example 1. A homogeneous solution was prepared by adding 20 ml of water to 995 mg of lithium dibutyldithiocarbamate (5 millimols), followed by addition of 5 ml of carbon disulfide. Electrolytic reaction was carried out with stirring at a reaction temperature of 18° to 20° C. under the conditions of a terminal voltage of 2 V and a current density of 10 to 5 mA/cm². Every time a quantity of electricity of $0.5 \times 10^{-3}$F was passed, the lower layer of the reaction system was taken out, and 65 mg (0.5 millimol) of dibutylamine and 3 ml of carbon disulfide was added to the aqueous solution of the upper layer, while the electrolysis was continued. The lower layer thus taken out was subjected to washing with water, dehydration and concentration to obtain 102 to 99 mg (100 to 97% yield) each time of the tetrabutylthiuram disulfide as a dark-brown viscous liquid having a solidifying point of 20° C. The operations was repeated 15 times to obtain a total of 1.51 g (98% yield) of tetrabutylthiuram disulfide. The resulting product was confirmed to be tetrabutylthiuram disulfide as a result of identification by thin-layer chromatography and IR and NMR absorption spectra as well as elemental analysis (as $C_{18}H_{28}N_2S_4$, Calculated: C 52.88%; H 8.89%; N 6.85%, Found: C 52.83%; H 8.90%; N 6.77%).

As clearly shown also in these examples, the process according to the present invention is a process for preparing tetraalkylthiuram disulfides in a high yield with simple reaction steps and without side reaction and is characterized in that: an alkali metal salt of dialkyldithiocarbamic acid is subjected to electrolytic oxidation in an electrolytic solution which is in a two liquid system comprising water and carbon disulfide, to directly produce tetraalkylthiuram disulfides; the by-product alkali metal hydroxide formed in the electrolytic reaction reacts with the corresponding dialkylamine and carbon disulfide which are added to the reaction system to produce the alkali metal salt of dialkyldithiocarbamic acid; and the alkali metal dialkyldithiocarbamate is thus supplied and the electrolytic reaction is continuously carried out.

What we claim is:

1. A process for preparing a tetraalkylthiuram disulfide, which comprises subjecting an alkali metal dialkyldithiocarbamate represented by the formula:

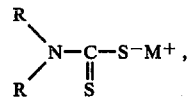

wherein R represents an alkyl group having 1 to 4 carbon atoms, and M is an alkali metal selected from the group consisting of sodium, potassium, and lithium, to electrolytic oxidation, whereby the carbamate is dimerized to form the corresponding tetraalkylthiuram disulfide, said electrolytic oxidation being conducted in the absence or presence of a supporting electrolyte in a two-layer electrolytic solution consisting essentially of an aqueous phase comprising water and a non-aqueous phase comprising carbon disulfide with electrodes in contact with the aqueous phase that contains the alkali metal dialkyldithiocarbamate dissolved therein, and allowing the resulting tetraalkylthiuram disulfide to be extracted by the non-aqueous phase.

2. The process as set forth in claim 1 in which the non-aqueous phase consists essentially of carbon disulfide.

3. The process as claimed in claim 1 in which the non-aqueous phase comprises a mixture of carbon disulfide as a predominant component of the mixture and a halogenated alkane having a higher density than water.

4. The process as set forth in claim 1 in which carbon disulfide and a dialkylamine corresponding to the alkali metal dialkyldithiocarbamate are gradually added to the aqueous layer, and an alkali metal hydroxide produced in the course of the electrolytic reaction reacts with the dialkylamine and carbon disulfide to form the corresponding alkali metal dialkyldithiocarbamate, whereby the resulting carbamate is successively supplied to the reaction system and the tetraalkylthiuram disulfide is continuously produced.

5. The process as set forth in claim 1 in which the electrodes are produced from the materials selected from the group consisting of platinum, carbon, titanium oxide and other electroconductive materials.

6. The process as set forth in claim 1, in which the electrolytic oxidation reaction is carried out at a terminal voltage of about 1.0 to 10 V.

7. The process as set forth in claim 1, in which the electrolytic oxidation reaction is carried out at a temperature of from about 5° to about 40° C.

8. The process as set forth in claim 7 in which the reaction temperature is approximately room temperature.

9. The process as set forth in claim 1 in which the halogenated alkane is employed in a quantity of from 0.1 to 20 times by volume that of the carbon disulfide.

10. The process as set forth in claim 1 in which the supporting electrolyte is selected from the group consisting of lithium perchlorate, magnesium perchlorate, quaternary alkylammonium perchlorates, quaternaly alkylammonium tetrafluoroborates, quaternary alkylammonium halides, alkyl metal halides, quaternary alkylammonium nitrates, and quaternary alkylammonium para-toluenesulfonates, wherein, the alkyl group is methyl, ethyl, propyl and butyl, the alkali metal is lithium, potassium and sodium, and the halogen is chlorine, bromine or iodine.

* * * * *